United States Patent

Sawatari et al.

[11] 4,008,274
[45] Feb. 15, 1977

[54] CERTAIN SALICYLANILIDES

[75] Inventors: Kenichi Sawatari; Toshihiko Mukai, both of Nakatsu; Satoshi Oda, Yoshitomi; Hiroyuki Akashi, Fukuoka; Masanori Kohara, Nakatsu, all of Japan

[73] Assignee: Yoshitomi Pharmaceutical Industries, Ltd., Osaka, Japan

[22] Filed: June 25, 1974

[21] Appl. No.: 482,916

[30] Foreign Application Priority Data

June 25, 1973 Japan .............................. 48-71969

[52] U.S. Cl. ...................... 260/559 S; 260/559 T; 424/230
[51] Int. Cl.² ....................................... C07C 103/26
[58] Field of Search ................................ 260/559 S

[56] References Cited
UNITED STATES PATENTS

| 1,903,899 | 4/1933 | Laska et al. | 260/559 S |
| 2,047,513 | 7/1936 | Laska et al. | 260/559 S |
| 3,649,637 | 3/1972 | Howes et al. | 260/559 S |

Primary Examiner—Paul M. Coughlan, Jr.
Attorney, Agent, or Firm—Sughrue, Rothwell, Mion, Zinn and Macpeak

[57] ABSTRACT

Salicylanilides of the formula:

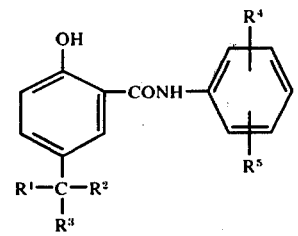

wherein each of $R^1$ and $R^2$ is hydrogen or methyl; $R^3$ is hydrogen or $C_{1-5}$ alkyl; $R^4$ is hydrogen, nitro or methyl; and $R^5$ is nitro, methyl, methoxy, ethoxy, methylthio or ethylthio, having utility as antifouling agents but having very low mammalian toxicity.

13 Claims, No Drawings

CERTAIN SALICYLANILIDES

The present invention relates to novel and useful halogen-free salicylanilides and antifouling compositions containing the same.

Antifouling agents are used to inhibit marine organisms such as sea-insects, sea-weeds, molluscs or shellfishes sticking to ship-bottoms, fishing nets, piers, submarine cables, intake or drain pipes using seawater as a coolant and other various underwater structures. Heretofore, on one hand, inorganic heavy metal compounds such as copper suboxide or mercury oxide as well as organometallic compounds such as organotin compounds or organoarsenic compounds have been used as antifouling agents. However, these heavy metal compounds may lead to environmental pollution. On the other, organic halogenated compounds such as 1,2,3,4,5,6-hexachlorocyclohexane (Lindane) and 1,1,1-trichloro-2,2-bis(p-chlorophenyl)ethane (DDT) have been used. These halogen-containing compounds also have a drawback that they can hardly be decomposed and may be accumulated in marine organisms. Therefore, it is highly desirable that such antifouling agents are available as are sufficiently effective against marine organisms but have very low mammalian toxicity and are safe in handling.

A number of salicylanilides are known to be biocides. Thus, for example, salicylanilide was proposed as antifouling agent in J. Iron Steel Inst. (London) 154, No. 2, 297p–333p (1946), but apparently is not in use. 3,4′,5-Tribromosalicylanilide (Tribromsalan) is used in detergents as a germicide. 2′,5-Dichloro-4′-nitrosalicylanilide (Niclosamide) is a molluscicide. 5-Alkyl-2′,4′-dihalosalicylanilides have bactericidal and fungicidal activities (British Patent No. 728098). 3-Tert-butyl-5-chloro-3′(5′)-nitrosalicylanilides are useful as bacteriostatic agents, lamprecides and selective fish poisons (German Patent Application No. 2053210). 3-Tert-butyl-2′,5-dihalo-4′-nitrosalicylanilides have utility as pesticides against Mollusca (Netherlandish Patent Application No. 6607810). These substituted salicylanilides contain halogen atoms as substituents.

3-Tert-butyl-6-methyl-5-nitrosalicylanilides are also known to be useful in the control of microorganisms and as insecticides (U.S. Pat. No. 3,801,637).

It has now been found that novel halogen-free salicylanilides of the formula:

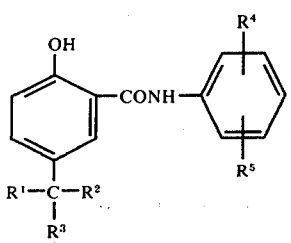

wherein each of $R^1$ and $R^2$ is hydrogen or methyl; $R^3$ is a member selected from the group consisting of hydrogen and an alkyl group having 1 to 5 carbon atoms (e.g. methyl, ethyl or neopentyl); $R^4$ is a member selected from the group consisting of hydrogen, nitro and methyl; and $R^5$ is a member selected from the group consisting of nitro, methyl, methoxy, ethoxy, methylthio and ethylthio are highly effective antifouling agents but have very low mammalian toxicity.

The compounds of formula [I] can be produced by reacting a compound of the formula:

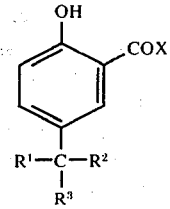

wherein each of $R^1$, $R^2$ and $R^3$ is as defined above and X is a member selected from the group consisting of hydroxyl, halogen (e.g. Cl or Br) and phenoxy, with a compound of the formula:

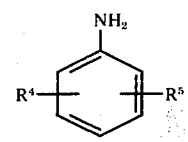

wherein each of $R^4$ and $R^5$ is as defined above.

Preferred salicylic acids of formula [II] are 5-methyl-, 5-isopropyl-, 5-tert-butyl- and 5-tert-amylsalicylic acid.

Preferred anilines of formula [III] include p-nitroaniline, 2-methyl-4-nitroaniline, 2-methyl-5-nitroaniline, 3-methyl-4-nitroaniline and 2,3-dimethylaniline. Other anilines such as m-nitroaniline, 2-methoxy-4-nitroaniline, p-methoxyaniline and m-methylthioaniline are also usable.

Preferably the reaction is carried out as follows:

Phosphorus trichloride, phosphorus pentachloride or phosphorus oxychloride is added dropwise to a mixture of a compound of formula [II] wherein X is hydroxyl and a compound of formula [III] in an inert solvent such as xylene or monochlorobenzene heated at about 60° to 70° C and then the mixture is heated at about 100° to 150° C for about 2 hours.

A compound of formula [II] wherein X is halogen is allowed to react with a compound of formula [III] in an inert solvent at about 100° to 150° C for about 7 to 10 hours.

Reaction of a compound of formula [II] wherein X is phenoxy with an aniline [III] is carried out at about 190° to 210° C under removal of by-product phenol from the reaction system.

The antifouling compositions of the present invention contain at least one member of the class consisting of the compounds of formula [I]. The compositions can take a form of solution or paint. Suitable solvents for the said solution include methanol, ethanol and acetone. The paint may contain a vehicle, a plasticizer, a solvent, and, if desired a pigment. The said vehicle is, for example, rosin, boiled oil, a chlorinated rubber, an alkyd resin, a vinyl resin [e.g. poly(vinyl chloride) or poly(vinyl acetate)], an acrylic resin, a polyolefin (e.g. polybutene), polystyrene, a synthetic rubber, a polyurethane resin, an amino resin, an epoxy resin, an unsaturated polyester resin, a phenolic resin, asphalt, coal-tar and the like. The plasticizer is, for example, dioctyl phthalate or tricresyl phosphate. Suitable solvents are ethanol, toluene, xylene, methyl isobutyl ketone, butyl acetate and mineral spirits. The pigments include titanium dioxide, red iron oxide and cyanine blue NC-1. The paint may also contain talc, a body pigment such as calcium carbonate, barium sulfate or aluminium silicate and a drier such as cobalt naphthenate or manganese naphthenate. The compositions may contain other known active ingredients.

The antifouling composition of the present invention may be applied to various materials to be protected the latter from marine organisms in a conventional method, for example, by spraying, immersing, brushing or mixing.

The present invention will be better understood from the following tests and examples, but they are not to be construed as limiting the present invention.

I. TEST COMPOUNDS

1: 2′,5-Dimethyl-4′-nitrosalicylanilide
2: 3′,5-Dimethyl-4′-nitrosalicylanilide
3: 2′,5-Dimethyl-5′-nitrosalicylanilide
4: 5-Methyl-4′-nitrosalicylanilide
5: 5-Methyl-3′-methylthiosalicylanilide
6: 2′-Methoxy-5-methyl-4′-nitrosalicylanilide
7: 2′-Methyl-4′-nitro-5-isopropylsalicylanilide
8: 2′-Methyl-5′-nitro-5-isopropylsalicylanilide
9: 4′-Nitro-5-isopropylsalicylanilide
10: 5-Tert-butyl-2′-methyl-4′-nitrosalicylanilide
11: 5-Tert-butyl-3′-methyl-4′-nitrosalicylanilide
12: 5-Tert-butyl-2′-methyl-5′-nitrosalicylanilide
13: 5-Tert-butyl-4′-nitrosalicylanilide
14: 5-Tert-butyl-3′-methylthiosalicylanilide
15: 5-Tert-butyl-2′-methoxy-4′-nitrosalicylanilide
16: 5-Tert-butyl-2′,3′-dimethylsalicylanilide
17: 5-Tert-butyl-4′-methoxysalicylanilide
18: 5-Tert-amyl-2′-methyl-4′-nitrosalicylanilide
19: 5-Tert-amyl-3′-methyl-4′-nitrosalicylanilide
20: 5-Tert-amyl-2′-methyl-5′-nitrosalicylanilide
21: 5-Tert-amyl-4′-nitrosalicylanilide
22: 5-Tert-amyl-3′-methylthiosalicylanilide
23: 5-Tert-amyl-2′-methoxy-4′-nitrosalicylanilide
24: 2′-Methyl-5-(1,1,3,3-tetramethylbutyl)-4′-nitrosalicylanilide

II. TEST METHODS

1. Algicidal Activity

Tap water (4 liters) was poured into a glass vessel (15 × 20 × 21 cm). The vessel was kept in a greenhouse maintained at 20°±2° C. Then 1 ml (or 5 ml) of a solution prepared by dissolving 0.400 g of the test compound in 100 ml of 4:1 ethanol-acetone mixture was dropped into the vessel to attain the concentration of 1 ppm (or 5 ppm). As the control run, 1 ml (or 5 ml) of the solvent was dropped into the vessel. About 5 g of wet Spirogyra was put in the vessel. Clean air was introduced at a rate of 150 ml/min for 48 hours.

The algicidal acticity was evaluated by the following criteria:
0: Brown algae on the bottom of the vessel. Destroyed and brown spiral chloroplasts (under a microscope).
10: Vigorous algae growth. Vivid green spiral chloroplasts (under a microscope).

The results are summerized in TABLE I.

TABLE I

| Test Compound | 1 ppm | 5 ppm |
|---|---|---|
| 1 | 0 | 0 |
| 2 | 0 | 0 |
| 4 | 10 | 0 |
| 7 | 0 | 0 |
| 8 | 10 | 0 |
| 9 | 0 | 0 |
| 10 | 0 | 0 |
| 11 | 10 | 0 |
| 12 | 10 | 0 |
| 14 | 10 | 0 |
| 16 | 10 | 0 |
| 17 | 10 | 0 |
| 18 | 0 | 0 |
| 19 | 0 | 0 |
| 20 | 0 | 0 |
| 21 | 0 | 0 |
| 22 | 10 | 0 |
| 23 | 0 | 0 |
| Control | 10 | 10 |

2. Barnacle Killing Activity

Seawater (4 liters) was poured into a glass vessel (15 × 20 × 21 cm). The water temperature was maintained at 20°±2° C. Clean air was introduced at a rate of 150 ml/min throughout the experiment. Then 1 ml (or 5 ml) of a solution prepared by dissolving 0.400 g of the test compound in 100 ml of 4:1 ethanol-acetone mixture was dropped into the vessel to attain the concentration of 1 ppm (or 5 ppm). As the control run, 1 ml (or 5 ml) of the solvent was dropped into the vessel. Of scores of barnacles sticking to a stone obtained from the sea-shore 30 living barnacles were selected at random, the rest of the barnacles on the stone being neglected for the experiment. Such stone was put in the vessel. After 48 hours, the number of dead barnacles was counted. The results are summerized in TABLE II.

TABLE II

| Test Compound | 1 ppm | 5 ppm |
|---|---|---|
| 1 | 10 | 30 |
| 2 | 2 | 30 |
| 3 | 3 | 30 |
| 5 | 2 | 18 |
| 6 | 2 | 20 |
| 7 | 14 | 30 |
| 8 | 16 | 30 |
| 9 | 20 | 30 |
| 10 | 30 | 30 |
| 11 | 30 | 30 |
| 12 | 30 | 30 |
| 13 | 22 | 30 |
| 14 | 3 | 30 |
| 15 | 9 | 30 |
| 16 | 4 | 30 |
| 18 | 30 | 30 |
| 19 | 2 | 30 |
| 20 | 30 | 30 |
| 21 | 25 | 30 |
| 23 | 6 | 30 |
| Control | 0 | 0 |

3. Antifouling Activity

An antifouling composition was applied to a net by immersion. The composition was composed of the following constituents:
15 parts by weight of the salicylanilide [1],
1.5 parts by weight of chlorinated rubber,
12.9 parts by weight of rosin,
1.6 parts by weight of titanium dioxide,
3 parts by weight of talc,
8.9 parts by weight of dioctyl phthalate, 1.4 parts by weight of cyanine blue NC-1,
30.7 parts by weight of xylene, and
25 parts by weight of butyl acetate.

Composition I contained as the salicylanilide 5-tert-butyl-2'-methyl-4'-nitrosalicylanilide (Test Compound 10), Composition II 5-tert-butyl-3'-methyl-4'-nitrosalicylanilide (Test Compound 11), Composition III 5-tert-butyl-2'-methyl-5'-nitrosalicylanilide (Test Compound 12) and Composition IV 5-tert-amyl-2'-methyl-4'-nitrosalicylanilide (Test Compound 18). The blank composition contained no salicylanilide. The net was made of cords of sixty 400-denier polyethylene filaments and had a size of 0.5 × 1 m, the mesh size being 3 × 3 cm.

After the immersion treatment the net was air-dried, and the percentage increase of weight was calculated according to the formula:

$$100 \times \left( \frac{\text{Weight of treated and air-dried net}}{\text{Weight of untreated net}} - 1 \right)$$

The values obtained were 22% for Composition I, 23% for Composition II, 23% for Composition III, 25% for Composition IV and 16% for the blank.

The net was immersed in Tsukumi-Bay, Oita, Japan at a depth of 1.5 m for the period of 3 months beginning in June and ending in September of 1973.

The net treated with Compositions I to IV remained free from fouling organisms after the 3 months' immersion, while the net treated with the blank composition was crowded with marine organisms such as lavers, acsidians and bryozoans in the first 1 month.

4. Antibacterial Activity

The minimal inhibitory concentration (MIC; mcg/ml) of the test compounds determined by the agar dilution method on the nutrient agar medium is shown in TABLE III.

The procedure is as follows: The test compound was mixed with the nutrient agar medium and the medium was allowed to coagulate. A solution containing *Staphylococcus aureus* FDA 2099 or *Bacillus subtilis* PCI 219 was inoculated into the medium and cultivated at 37° C for 2 days.

TABLE III

| Test Compound | Staphylococcus aureus FDA 2099 | Bacillus subtilis PCI 219 |
|---|---|---|
| 1 | 5 | 2 |
| 3 | 10 | 10 |
| 7 | 5 | 5 |
| 8 | 5 | 5 |
| 9 | 5 | 5 |
| 10 | 1 | 0.5 |
| 11 | 1 | 1 |
| 12 | 2 | 2 |
| 13 | 2 | 1 |
| 14 | 5 | 5 |
| 18 | 0.5 | 0.5 |
| 19 | 0.5 | 0.5 |
| 20 | 1 | 1 |
| 21 | 1 | 1 |
| 23 | 5 | 5 |
| 24 | 1 | 1 |

5. Toxicity a. Oral toxicity

Oral LD$_{50}$ values were determined in dd-strain female mice according to the conventional Litchfield-Wilcoxon method. The test compound was administered as a 25% suspension in water containing 0.5% carboxymethylcellulose.

b. Percutaneous toxicity

Percutaneous LD$_{50}$ values were determined in dd-strain female mice by applying a 10% solution of the test compound in acetone on the shaved backs.

The results are summarized in TABLE IV.

TABLE IV

|  | Oral LD$_{50}$ (mg/kg) | Percutaneous LD$_{50}$ (mg/kg) |
|---|---|---|
| Test Compound 10 | >>10000 | >>5000 |
| Test Compound 16 | >>10000 | >>5000 |
| Tribromsalan | 124 | >2000 |

EXAMPLE 1

5-Tert-butyl-2'-methyl-4'-nitrosalicylanilide

A solution of 9.7 g of 5-tert-butylsalicylic acid and 7.6 g of 2-methyl-4-nitroaniline in 120 ml of xylene is heated at 65° to 70° C. To a reaction solution is added a solution of 2.6 g of phosphorus trichloride in 30 ml of xylene. The whole mixture is refluxed for 2 hours. The hot reaction solution is decanted. The supernatant solution is cooled on an ice bath. The crystalline precipitate is collected by filtration. Recrystallization from methanol gives 11.5 g of the title compound as pale yellow needles, melting at 202°–204° C.

EXAMPLE 2

5-Tert-amyl-2'-methyl-4'-nitrosalicylanilide

A mixture of 10.4 g of 5-tert-amylsalicylic acid and 7.6 g of 2-methyl-4-nitroaniline in 100 ml of xylene is heated at 70° C and to the mixture is added a solution of 2.6 g of phosphorus trichloride in 10 ml of xylene. The whole mixture is refluxed for two and a half hours. The hot reaction solution is decanted. The supernatant solution is cooled on an ice bath. The crystalline precipitate is collected by filtration. Recrystallization from methanol gives 9.4 g of the title compound as pale yellow crystals, melting at 150°–151° C.

Using the procedure set forth in the above examples, but substituting equivalent amounts of the appropriate starting compounds, the following compounds are also produced.

2',5-Dimethyl-4'-nitrosalicylanilide, M.p. 216°–216.5° C;

3',5-Dimethyl-4'-nitrosalicylanilide, M.p. 202°–203° C;

2',5-Dimethyl-5'-nitrosalicylanilide, M.p. 210°–211° C;

5-Methyl-4'-nitrosalicylanilide; M.p. 236.5°–237° C;

5-Methyl-3'-methylthiosalicylanilide, M.p. 162.5°–163.5° C;

2'-Methoxy-5-methyl-4'-nitrosalicylanilide, M.p. 218°–219° C;

4'-Ethoxy-5-methylsalicylanilide;

2'-Methyl-4'-nitro-5-isopropylsalicylanilide, M.p. 175°–176° C;

2'-Methyl-5'-nitro-5-isopropylsalicylanilide, M.p. 126°–127° C;

4'-Nitro-5-isopropylsalicylanilide, M.p. 193.5°–194.5° C;

5-Tert-butyl-2'-methyl-5'-nitrosalicylanilide, M.p. 169°–171° C;

5-Tert-butyl-3'-methyl-4'-nitrosalicylanilide, M.p. 194°–195° C;
5-Tert-butyl-3'-methylthiosalicylanilide, M.p. 139°–140° C;
5-Tert-butyl-2',3'-dimethylsalicylanilide, M.p. 175°–176.5° C;
5-Tert-butyl-2'-methoxy-4'-nitrosalicylanilide, M.p. 213°–214° C;
5-Tert-butyl-2'-methoxy-5'-nitrosalicylanilide, M.p. 188°–190° C;
5-Tert-butyl-4'-methoxysalicylanilide, M.p. 151°–152° C;
5-Tert-butyl-4'-nitrosalicylanilide, M.p. 218°–219° C;
5-Tert-butyl-3'-nitrosalicylanilide, M.p. 191°–193° C;
5-Tert-butyl-4'-methyl-3'-nitrosalicylanilide, M.p. 219°–221° C;
5-Tert-butyl-3'-methyl-2'-nitrosalicylanilide;
5-Tert-butyl-4'-ethoxysalicylanilide;
5-Tert-butyl-4'-ethylthiosalicylanilide;
5-Tert-amyl-2'-methyl-4'-nitrosalicylanilide, M.p. 150°–151° C;
5-Tert-amyl-3'-methyl-4'-nitrosalicylanilide, M.p. 102°–104° C;
5-Tert-amyl-2'-methyl-5'-nitrosalicylanilide, M.p. 161°–162° C;
5-Tert-amyl-4'-nitrosalicylanilide, M.p. 200°–202° C;
5-Tert-amyl-3'-methylthiosalicylanilide, M.p. 94.5°–95° C;
5-Tert-amyl-2'-methoxy-4'-nitrosalicylanilide, M.p. 175°–176° C;
5-Tert-amyl-4'-ethoxysalicylanilide;
2'-Methyl-5-(1,1,3,3-tetramethylbutyl)-4'-nitrosalicylanilide;
3'-Methyl-5-(1,1,3,3-tetramethylbutyl)-4'-nitrosalicylanilide;
2'-Methyl-5-(1,1,3,3-tetramethylbutyl)-5'-nitrosalicylanilide, M.p. 201°–202° C;
5-(1,1,3,3-Tetramethylbutyl)-4'-nitrosalicylanilide, M.p. 196°–196.5° C;
5-(1,1,3,3-Tetramethylbutyl)-4'-nitrosalicylanilide, M.p. 196°–196.5° C;
5-(1,1,3,3-Tetramethylbutyl)-3'-methylthiosalicylanilide, M.p. 123.5°–124° C;
2'-Methoxy-5-(1,1,3,3-tetramethylbutyl)-4'-nitrosalicylanilide M.p. 209°–209.5° C.

What is claimed is:
1. The compound 2',5-Dimethyl-4'-nitrosalicylanilide.
2. The compound 3',5-Dimethyl-4'-nitrosalicylanilide.
3. The compound 2'-Methyl-4'-nitro-5-isopropylsalicylanilide.
4. The compound 2'-Methyl-5'-nitro-5-isopropylsalicylanilide.
5. The compound 4'-Nitro-5-isopropylsalicylanilide.
6. The compound 5-Tert-butyl-2'-methyl-4'-nitrosalicylanilide.
7. The compound 5-Tert-butyl-3'-methyl-4'-nitrosalicylanilide.
8. The compound 5-Tert-butyl-2'-methyl-5'-nitrosalicylanilide.
9. The compound 5-Tert-amyl-2'-methyl-4'-nitrosalicylanilide.
10. The compound 5-Tert-amyl-3'-methyl-4'-nitrosalicylanilide.
11. The compound 5-Tert-amyl-4'-nitrosalicylanilide.
12. The compound 5-Tert-amyl-2'-methyl-5'-nitrosalicylanilide.
13. The compound 5-Tert-amyl-2'-methoxy-4'-nitrosalicylanilide.

* * * * *